United States Patent
Qian

(10) Patent No.: US 7,498,367 B2
(45) Date of Patent: Mar. 3, 2009

(54) ACID-TOLERANT DENTAL COMPOSITION

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 321 days.

(21) Appl. No.: 10/906,447

(22) Filed: Feb. 21, 2005

(65) Prior Publication Data

US 2006/0189728 A1 Aug. 24, 2006

(51) Int. Cl.
- *C08K 5/34* (2006.01)
- *C08K 3/40* (2006.01)
- *C08K 3/08* (2006.01)
- *C08L 33/00* (2006.01)
- *C08L 31/00* (2006.01)

(52) U.S. Cl. .................. 524/99; 524/494; 524/432; 524/556; 524/558

(58) Field of Classification Search ............... 524/99, 524/494, 432, 556, 558
See application file for complete search history.

(56) References Cited

U.S. PATENT DOCUMENTS

| | | | |
|---|---|---|---|
| 3,991,008 A | 11/1976 | Temin et al. | |
| 4,567,030 A | 1/1986 | Yuasa et al. | 423/326 |
| 4,569,976 A * | 2/1986 | Zimmerman et al. | 526/204 |
| 4,775,585 A | 10/1988 | Hagiwara et al. | 428/323 |
| 4,792,632 A | 12/1988 | Ellrich et al. | 568/15 |
| 4,911,899 A | 3/1990 | Hagiwara et al. | 423/118 |
| 5,609,675 A | 3/1997 | Noritake et al. | 106/35 |
| 6,353,041 B1 * | 3/2002 | Qian | 523/116 |
| 6,495,643 B1 * | 12/2002 | Evans et al. | 526/256 |
| 2003/0114554 A1 * | 6/2003 | Ario et al. | 523/116 |
| 2003/0134933 A1 * | 7/2003 | Jin et al. | 523/115 |
| 2004/0014009 A1 * | 1/2004 | Jia et al. | 433/215 |
| 2004/0192805 A1 * | 9/2004 | Finger | 523/116 |
| 2004/0235981 A1 | 11/2004 | Qian | 523/115 |
| 2005/0226913 A1 * | 10/2005 | Bringley et al. | 424/443 |

FOREIGN PATENT DOCUMENTS

| | | |
|---|---|---|
| EP | 1479364 A1 | 11/2004 |
| EP | 1502569 A1 | 2/2005 |
| WO | WO0222041 A1 * | 3/2002 |

OTHER PUBLICATIONS http://www.thejcdp.com/issue036/garcia/03_page.htm, Aug. 15, 2000, vol. 08 (7), 048.*

European Search Report EP06 25 0900 mailed May 18, 2006.

* cited by examiner

*Primary Examiner*—Vasu Jagannathan
*Assistant Examiner*—Karuna P Reddy
(74) *Attorney, Agent, or Firm*—Wood Herron & Evans LLP

(57) ABSTRACT

A dental composition compatible with acidic dental primers/adhesives, the dental composition comprising (A) 5% (w/w) to 90% (w/w) of at least one polymerizable monomer having at least one ethylenically unsaturated vinyl, acrylate, or methacrylate group; (B) 0.01% (w/w) to 10% (w/w) of at least one compound of structure

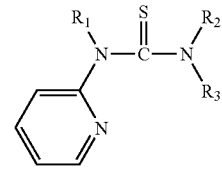

where each of R1, R2, and R3 may be the same or different and is independently selected from H, alkyl, alkoxyl, aryl, acyl, allyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one hydroperoxide groups attached to a tertiary carbon; (D) 5% (w/w) to 95% (w/w) of at least one finely divided filler; (E) 0% (w/w) to 25% (w/w) of one or more components selected from a solvent, a photoinitiator, a stabilizer, and/or an antimicrobial agent. One embodiment of the invention is a dental cementation or core buildup kit that has enhanced compatibility between the acidic primer/adhesive and the cement or core buildup material, and therefore enhanced adhesion to a tooth. The kit includes (I) an acidic primer/adhesive composition having a pH less than 4.5; and (II) a cement or core buildup material having the above described composition comprising components (A)-(E). Another embodiment of the invention is a method for adhering a prosthetic device to a tooth to restore the function and/or appearance of a diseased tooth. Another embodiment of the invention is a method of providing a temporary cement, crown and/or bridge, inlay, onlay, endodontic sealer, and/or an endodontic filling material, using the inventive composition.

52 Claims, No Drawings

ACID-TOLERANT DENTAL COMPOSITION

FIELD OF THE INVENTION

The invention is directed to dental compositions in general, and an acid tolerant dental composition in particular, kits containing the composition, and methods of using the composition.

BACKGROUND

Resin cement is increasingly being used as a dental luting material for cementing prosthetic devices to a tooth, due to its excellent mechanical properties and good optical properties. Resin cement has good translucency and good initial color-matching to a tooth's natural color. Cementing prosthetic devices such as veneers, inlays, onlays, crowns, bridges, and posts to a tooth using a resin cement involves the steps of (1) preparing the tooth (cutting and cleaning) to receive the prosthetic device; (2) optionally, etching the prepared tooth surface with an acidic etchant and rinsing to remove the etchant; (3) applying an acidic primer/adhesive to the tooth surface receiving the prosthetic device; (4) adhering the prosthetic device to the primer/adhesive coated tooth surface using a resin cement, and (5) hardening the dental cement. Adhesion of the prosthetic device depends on the extent of curing of the primer/adhesive and cement. When cementing metal-based or high opacity prosthetic devices, it is difficult for light to reach the adhesive and cement, so a photocure process cannot be used. Instead, a redox initiator system must be used for the cement to cure effectively in the dark without the need for light.

Current resin cements use benzoyl peroxide (BPO) and a tertiary amine as the redox initiator system to initiate polymerization and cure the cement. The resin cement typically comprises a base paste containing the tertiary amine and a catalyst paste containing BPO. When the base and catalyst pastes are mixed, BPO and the tertiary amine form a redox pair generating free radicals and initiating polymerization of the methacrylate monomers, causing the cement to harden (cure).

Most primer/adhesives, particularly self-etching primer/adhesive systems, are acidic. When a resin cement containing a BPO/tertiary amine initiator system is applied to a tooth coated with such an acidic primer/adhesive, the tertiary amine is quickly neutralized by the acidic primer/adhesive, thereby compromising its curing efficacy and resulting in poor adhesion at the primer/cement interface. The incompatibility of current resin cements with acidic primers/adhesives has been reported (King et al, Incompatibility Profiles of All-In-One Adhesives. I. True vs Apparent Incompatibility., International Association for Dental Research 82nd General Session, Abstract No. 23, Mar. 10-13, 2004, Honolulu, Hi.). This same incompatibility also exists between a core buildup material and an acidic primer/adhesive.

A redox initiator system that can tolerate the acidity of the primer/adhesive and that cures effectively at the interface between a cement and the acidic primer/adhesive is desirable. One such redox initiator system utilizes 1-(2-pyridyl)-2-thiourea and a tertiary hydroperoxide in a self-adhering dental composition (Qian U.S. Published patent application Ser. No. 10/440,804). This composition was applied directly to the tooth without any pre-treatment (etching or priming) of the tooth surface, but the bond strength was low without a primer/adhesive.

Other compositions are thus desirable.

SUMMARY OF THE INVENTION

One embodiment of the invention is a two-part dental composition comprising (A) 5% (w/w) to 90% (w/w) of at least one polymerizable monomer having at least one ethylenically unsaturated group selected from the group consisting of vinyl, acrylate and methacrylate; (B) 0.01% (w/w) to 10% (w/w) of at least one compound of structure

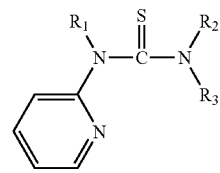

where each of R1, R2, and R3 may be the same or different and is independently selected from the group consisting of H, alkyl, alkoxyl, aryl, acyl, alyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one hydroperoxide group attached to a tertiary carbon; (D) 5% (w/w) to 95% (w/w) of at least one finely divided filler; and (E) 0% (w/w) to 25% (w/w) of at least one component selected from the group consisting of a solvent, a photoinitiator, a stabilizer, an antimicrobial agent, or combinations thereof, wherein component (B) is in a first part of the two-part composition, component (C) is in a second part of the two-part composition, and components (A), (D), and (E) are independently in either the first part and/or the second part of the composition. Each of R1, R2, and R3 of component (B) is independently selected from the group consisting of H, alkyl, phenyl, 2-pyridyl, 2-tetrahydrofufuryl, acetyl, and benzoyl. The hydroperoxide compound is selected from the group consisting of t-butyl hydroperoxide, t-amyl hydroperoxide, p-diisopropylbenzene hydroperoxide, cumene hydroperoxide, pinane hydroperoxide, p-menthane hydroperoxide, 1,1,3,3-tetramethylbutyl hydroperoxide, and combinations thereof. The filler is selected from the group consisting of inorganic metal, salt, oxide, nitride, silicate glass, bariumaluminosilicate glass, bariumaluminoborosilicate glass, strontiumaluminosilicate glass, bariumfluoroaluminosilicate glass, strontiumfluoroaluminosilicate glass, strontiumzincfluoroaluminosilicate glass, zincaluminosilicate glass, quartz, colloidal silica, precipitated silica, zirconia-silica, polymeric filler, polymerized composite filler with inorganic particles, and combinations thereof. In one embodiment, the concentration of the filler provides a radiopacity of the composition that is at least 100% of that of aluminum. The antimicrobial agent is selected from the group consisting of benzakonium chloride, triclosan, alkyl 4-hydroxybenzoate, zinc oxide, a silicate glass powder containing silver and/or zinc, a zeolite containing silver and/or zinc ion(s), and combinations thereof. Each part of the two-part composition is independently selected from the group consisting of a liquid, a powder, and a paste.

Another embodiment of the invention is a two-part paste/paste dental composition. The first paste comprises (A1) 10% (w/w) to 80% (w/w) of at least one polymerizable monomer having at least one ethylenically unsaturated group selected from the group consisting of vinyl, acrylate, and methacrylate; (B) 0.01% (w/w) to 10% (w/w) of at least one compound of structure

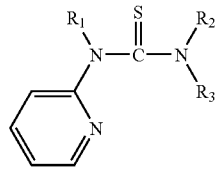

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; and (D1) 15% (w/w) to 90% (w/w) of at least one finely divided filler; and the second paste comprises (A2) 10% (w/w) to 80% (w/w) of at least one polymerizable monomer having at least one ethylenically unsaturated group selected from the group consisting of vinyl, acrylate, and methacrylate; (C) 0.01% (w/w) to 10% (w/w) of at least one hydroperoxide compound with at least one hydroperoxide group attached to a tertiary carbon; and (D2) 15% (w/w) to 90% (w/w) of at least one finely divided filler, wherein components (A1) and (A2) of the composition are the same or different, and the dental composition optionally further comprises 0% (w/w) to 25% (w/w) of a component selected from the group consisting of a photoinitiator, a stabilizer, a solvent, an antimicrobial agent, and combinations thereof.

Another embodiment of the invention is a two-part powder/liquid dental composition. The liquid comprises (A) 20% (w/w) to 99.5% (w/w) of at least one polymerizable monomer having at least one ethylenically unsaturated group selected from the group consisting of vinyl, acrylate, and methacrylate; and (C) 0.01% (w/w) to 10% (w/w) of at least one hydroperoxide compound with at least one hydroperoxide group attached to a tertiary carbon; and the powder comprises (B) 0.01% (w/w) to 10% (w/w) of at least one compound of structure

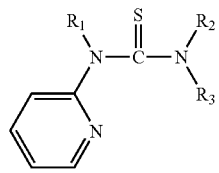

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; (D) 50% (w/w) to 99.5% (w/w) of at least one finely divided filler; and the dental composition optionally further comprises 0% (w/w) to 25% (w/w) of a component selected from the group consisting of a photoinitiator, a stabilizer, a solvent, an antimicrobial agent, and combinations thereof.

Another embodiment of the invention is a dental cementation or core buildup kit. The kit comprises (I) a primer/adhesive composition having a pH less than 4.5; and (II) a two-part dental cement or core buildup material composition comprising (A) 5% (w/w) to 90% (w/w) of at least one polymerizable monomer having at least one ethylenically unsaturated group selected from the group consisting of vinyl, acrylate, and methacrylate; (B) 0.01% (w/w) to 10% (w/w) of at least one compound of structure

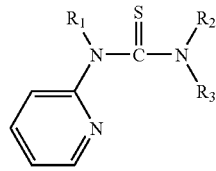

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one hydroperoxide group attached to a tertiary carbon; (D) 5% (w/w) to 95% (w/w) of at least one finely divided filler; (E) 0% (w/w) to 25% (w/w) of at least one component selected from the group consisting of a solvent, a photoinitiator, a stabilizer, an antimicrobial agent, and combinations thereof, wherein component (B) is in a first part of the two-part composition, component (C) is in a second part of the two-part composition, and components (A), (D), and (E) are independently in either the first part and/or the second part. The two-part dental cement or core buildup material composition may be provided in a prepackaged container such as a syringe, bottle, capsule, ampule, or jar. Each part of the two-part dental cement or core buildup material composition independently may be a paste, a powder, or a liquid. In one embodiment, the prepackaged container is a dual-syringe assembly with each syringe housing one part of the two-part composition. A static mixer is attached to the openings of the dual syringe to provide a homogeneous mixture upon dispensing the mixed composition. In one embodiment, the prepackaged container is a single-dose assembly with the two parts of the two-part composition not in contact with each other.

Another embodiment of the invention is a method for adhering a prosthetic device to a tooth. A primer/adhesive with a pH less than 4.5 is applied to a surface of a tooth prepared to receive the device. The prosthetic device is adhered using a dental cement, and the dental cement is hardened. The dental cement composition comprises (A) 5% (w/w) to 90% (w/w) of at least one polymerizable monomer having at least one ethylenically unsaturated group selected from the group consisting of vinyl, acrylate, and methacrylate; (B) 0.01% (w/w) to 10% (w/w) of at least one compound of structure

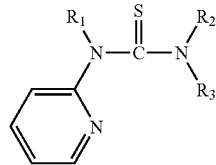

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one hydroperoxide group attached to a tertiary carbon; (D) 5% (w/w) to 95% (w/w) of at least one finely divided filler; (E) 0% (w/w) to 25% (w/w) of at least one component selected from the group consisting of a solvent, a photoinitiator, a stabilizer, an antimicrobial agent, and combinations thereof, wherein component (B) is in a first part of the two-part composition, component (C) is in a second part of the two-part composition, and components (A), (D), and (E) are independently in either the first part and/or the second part.

In the method, an acidic etchant many optionally be applied to the tooth surface and then rinsed off prior to the first step.

Another embodiment of the invention is a method for providing a tooth with a dental composition. A composition comprising (A) 5% (w/w) to 90% (w/w) of at least one polymerizable monomer having at least one ethylenically unsaturated group selected from the group consisting of vinyl, acrylate, and methacrylate; (B) 0.01% (w/w) to 10% (w/w) of at least one compound of structure

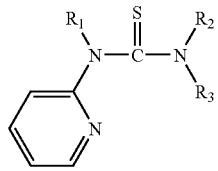

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one hydroperoxide group attached to a tertiary carbon; (D) 5% (w/w) to 95% (w/w) of at least one finely divided filler; (E) 0% (w/w) to 25% (w/w) of at least one component selected from the group consisting of a solvent, a photoinitiator, a stabilizer, an antimicrobial agent, or combinations thereof; wherein component (B) is in a first part of the two-part composition, component (C) is in a second part of the two-part composition, and components (A), (D), and (E) are independently in either the first part and/or the second part, the components mixed substantially immediately before application to the tooth, is applied to a tooth prepared to receive the composition, and the composition is then hardened. This method may be used to provide a permanent cement, a core buildup material, a filling material, a temporary cement, a temporary crown and/or bridge, a temporary inlay, a temporary onlay, an endodontic sealer, or an endodontic filling material to the tooth.

These and other advantages will be apparent in light of the following figures and detailed description.

DETAILED DESCRIPTION

One embodiment of the invention is an acid tolerant dental composition compatible with acidic dental primers/adhesive. The composition is described as acid tolerant in that the initiator component does not degrade in the presence of acid, so that curing of the composition is not affected by the acidity of the primer/adhesive with which the composition comes in contact. The composition thus enhances adhesion of prosthetic devices applied to a primer/adhesive coated tooth.

The composition comprises (A) 5% (w/w) to 90% (w/w) of at least one polymerizable monomer having at least one ethylenically unsaturated group, either vinyl, acrylate, or methacrylate; (B) 0.01% (w/w) to 10% (w/w) of at least one compound of structure

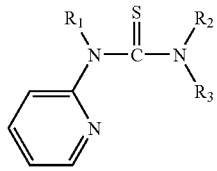

where each of R1, R2, and R3 may be the same or different and is independently selected from H, alkyl, alkoxyl, aryl, acyl, allyl, pyridyl, —OH, alkenyl, aralkyl, cycloalkyl, and heterocyclic structure containing O, S, or N; (C) 0.01% (w/w) to 10% (w/w) of at least one hydroperoxide compound with at least one of the hydroperoxide groups attached to a tertiary carbon; (D) 5% (w/w) to 95% (w/w) of at least one finely divided filler; and (E) 0% (w/w) to 25% (w/w) of one, or a combination of, a solvent, a photoinitiator, a stabilizer, and/or an antimicrobial agent.

In another embodiment, the invention is directed to a dental cementation or core buildup kit with enhanced compatibility between an acidic primer/adhesive and the cement or core buildup material, therefore improving adhesion to the tooth. The kit includes (I) an acidic primer/adhesive composition having a pH less than 4.5; and (II) a cement or core buildup composition having components (A)-(E) as previously described.

In another embodiment, the invention is directed to a method for adhering a prosthetic device to a tooth to restore the function and/or appearance of a diseased tooth. A prosthetic device includes, but is not limited to, a dental crown, bridge, inlay, onlay, veneer, or post. The diseased tooth is prepared (e.g., cleaned, cut, trimmed, etc.) to receive the device. In some embodiments, an acidic etchant is applied to the surface of the tooth to which the device will be applied, and then the etchant is removed by rinsing the surface. A primer/adhesive with a pH less than 4.5 is applied to this surface, to which the prosthetic device is adhered using the cement composition having components (A)-(E) as previously described.

The inventive dental cement or core buildup composition tolerates the acidic primer/adhesive already coated on the tooth surface. In one embodiment, the inventive composition enhances adhesion of a prosthetic device applied to the primer/adhesive coated tooth surface. In another embodiment, the inventive composition is a temporary cement, temporary crown and/or bridge, a temporary inlay, a temporary onlay, an endodontic sealer, and/or an endodontic filling material.

For component (A), at least one polymerizable monomer can be used. Examples of the polymerizable monomer include, but are not limited to, the following: hydroxyethyl (meth)acrylate {(meth)acrylate=acrylate or methacrylate}, hydroxypropyl (meth)acrylate, hydroxybutyl (meth)acrylate, glycerol di(meth)acrylate, glycerol mono(meth)acrylate, methyl (meth)acrylate, ethyl (meth)acrylate, propyl (meth)acrylate, butyl (meth)acrylate, hexyl (meth)acrylate, octyl (meth)acrylate, lauryl (meth)acrylate, decyl (meth)acrylate, tridecyl (meth)acrylate; 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth)acrylate (TEGDMA), tetraethyleneglycol di(meth)acrylate, polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, trimethylolpropane tri(meth)acrylate, ethoxylated trimethylolpropane tri(meth)acrylate, UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate (EB-PADMA-n where n=total number of moles of ethylene oxide in the molecule, as only one example, n=2-20 units), tetrahydrofurfuryl (meth)acrylate, or mixtures thereof. In one embodiment, polymerizable monomers containing hydroxyl functional groups are used. Examples of hydroxyl-containing polymerizable monomers include, but are not limited to, hydroxyethyl (meth)acrylate, hydroxypropyl (meth)acrylate, hydroxybutyl (meth)acrylate, glycerol di(meth)acrylate, glycerol mono(meth)acrylate, 2,2-bis[4-(2-hydroxy-3-methacryloylpropoxy)-phenyl]-propane (Bis-GMA). In one embodiment, polymerizable monomers containing at least one acidic group are used. The acidic group may be carboxylic acid, carboxylic acid anhydride, sulfonic acid, sulfinic acid, phosphoric acid, a phosphoric acid derivative, phosphonic acid, or a phosphonic acid derivative, with a derivative being a salt or ester of the respective acid. In one embodiment, the acidic group is phosphoric acid and its derivatives, and/or phosphonic acid and its derivatives. The concentration of total polymerizable monomers (A) is in the range of about 5% (w/w) to about 90% (w/w) of the composition. In one embodiment, the concentration of total polymerizable monomers (A) is in the range of about 15% (w/w) to about 80% (w/w) of the composition. In one embodiment, the concentration of total polymerizable monomers (A) is in the range of about 20% (w/w) to about 50% (w/w) of the composition.

For component (B), at least one compound of the structure

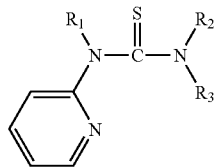

is incorporated, where each of R1, R2, and R3 may be the same or different and is independently selected from H, alkyl, alkoxyl, aryl, acyl, allyl, pyridyl, —OH, alkenyl, aralkyl, cycloalkyl, and a heterocyclic structure containing O, S, or N. Examples of component (B) include, but are not limited to, 1-benzoyl-3-(2-pyridyl)-2-thiourea, 1-acetyl-3-(2-pyridyl)-2-thiourea, 1-phenyl-3-(2-pyridyl)-2-thiourea, 1-(2-pyridyl)-2-thiourea, 1,3-di-(2-pyridyl)-2-thiourea, 1,1-dimethyl-3-(2-pyridyl)-2-thiourea, 1,1,3-trimethyl-3-(2-pyridyl)-2-thiourea, and 1-(2-tetrahydrofufuryl)-3-(2-pyridyl)-2-thiourea. Each of R1, R2, and R3 can be up to C14 structures. The concentration of component (B) is in the range of about 0.01% (w/w) to about 10% (w/w) of the composition. In one embodiment, the concentration of component (B) is in the range of about 0.05% (w/w) to about 2% (w/w) of the composition. In one embodiment, the concentration of component (B) is in the range of about 0.10% (w/w) to about 1% (w/w) of the composition.

For component (C), any hydroperoxide compound that has at least one hydroperoxide group attached to a tertiary carbon can be used. The hydroperoxide compound can contain more than one hydroperoxide group. Examples of tertiary hydroperoxide compounds include, but are not limited to, t-butyl hydroperoxide, t-amyl hydroperoxide, p-diisopropylbenzene hydroperoxide, cumene hydroperoxide, pinane hydroperoxide, p-menthane hydroperoxide, and 1,1,3,3-tetramethylbutyl hydroperoxide. The concentration of component (C) ranges from about 0.01% (w/w) to about 10% (w/w) of the composition. In one embodiment, the concentration of component (C) ranges from about 0.1% (w/w) to about 5% (w/w) of the composition.

For component (D), at least one filler is incorporated into the composition. Fillers enhance mechanical properties of the composition, reduce polymerization shrinkage, improve rheological properties of the composition, and increase radiopacity of the composition for ease in detection of gaps or voids. Examples of fillers include, but are not limited to, inorganic metal, salt, oxide, nitride, silicate glass, aluminosilicate glass, aluminoborosilicate glass, fluoroaluminosilicate glass, quartz, colloidal silica, precipitated silica, zirconia-silica, polymeric filler, and/or polymerized composite fillers with inorganic particles. In one embodiment, inorganic fillers for increased x-ray contrast ability include metals, salts, oxides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, yttrium fluoride, barium tungstate, zinc oxide, bismuth (III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, etc. Fumed silica, colloidal silica, or precipitated silica can also be incorporated to improve the dispersion of the filler, as well as the rheological and handling properties of the composition. Examples of colloidal silicas are Aerosil series such as OX-50, OX-130, and OX-200 silica sold by Degussa (Ridgefield Park, N.J.), and Cab-O-Sil M5 and Cab-O-Sil TS-530 silica sold by Cabot Corp (Tuscola, Ill.). The filler also includes nanoparticles such as those obtained through a sol-gel process. Examples include those disclosed in U.S. Pat. Nos. 4,567,030 and 5,609,675, the disclosure of each expressly incorporated by reference herein in its entirety. Mixtures of different fillers can be used. For inorganic fillers, the surface of the filler may be treated or coated with a coupling agent, such as gamma-methacryloyloxypropyltrimethoxy-silane (MPTMS), that enhances the interfacial bonding between the filler and resin matrix and improves mechanical properties. In one embodiment, the mean particle size of the filler is less than 50 microns. In another embodiment, the mean particle size of the filler is less than 10 microns. The concentration of total filler(s) ranges from about 10% (w/w) to about 95% (w/w) of the composition. In one embodiment, the concentration of total filler(s) ranges from about 30% (w/w) to about 80% (w/w) of the composition. In one embodiment, the concentration of filler is sufficient to provide radiopacity of the composition to be equal to or greater than 100% of aluminum.

For component (E), 0% (w/w) to 25% (w/w) of one or more of the following components may be present in the composition: a solvent (E1), a photoinitiator system (E2), a stabilizer (E3), and/or an antimicrobial agent (E4).

In one embodiment, a solvent (E1) may be present at a concentration of 0% (w/w) to about 20% (w/w) of the composition. In another embodiment, a solvent may be present at a concentration of 0% (w/w) to about 10% (w/w) of the composition. Solvents that may be used include water, methanol, ethanol, isopropanol, acetone, methyl ethyl ketone, ethylene glycol, and/or glycerin.

In one embodiment, a photoinitiator system (E2) may be present at a concentration of 0% (w/w) to about 10% (w/w) of the composition. In another embodiment, a photoinitiator system may be present at a concentration of 0% (w/w) to about 5% (w/w) of the composition. The inclusion of a photoinitiator system can render the composition dual-curable, i.e. both self-curable (in the absence of light) and photocurable. Examples of photoinitiators include, but are not limited to, benzoin, benzoin ethers and esters, 2,2-diethoxy acetophenone, diketone compounds such as camphorquinone and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photoinitiators. Additionally, an activator can be used together with a photoinitiator to enhance curing efficiency. Activators include tertiary amine and sulfinate compounds. Examples of activators include, but are not limited to, ethyl 4-(N,N-dimethylamino) benzoate, 2-(ethylhexyl)-4-(N,N-dimethylamino) benzoate, N,N-dimethylaminoethyl methacrylate, N,N-dimethylaminophenethyl alcohol, sodium benzenesulfinate, and sodium toluenesulfinate. In one embodiment, a photoinitiator system includes the combination of camphoroquinone and a tertiary amine such as ethyl 4-(N,N-dimethylamino) benzoate, 2-(ethylhexyl)-4-(N,N-dimethylamino) benzoate, N,N-dimethylaminoethyl methacrylate, and N,N-dimethylaminophenethyl alcohol. In another embodiment, a photoinitiator system includes the combination of camphoroquinone and bisacylphosphine oxide or monoacylphosphine oxide.

In one embodiment, a stabilizer (E3) is incorporated in the composition at a concentration of 0% (w/w) to about 5% (w/w) of the composition. In one embodiment, a stabilizer is incorporated in the composition at a concentration of 0% (w/w) to about 1% (w/w) of the composition. Stabilizers are polymerization inhibitors to improve the shelf stability of the composition. Examples of stabilizers include, but are not limited to, 2,6-di-(tert-butyl)-4-methylphenol (BHT) and 4-methoxyphenol (MEHQ).

In one embodiment, an antimicrobial agent (E4) may be present at a concentration of 0% (w/w) to about 20% (w/w) of the composition. In one embodiment, an antimicrobial agent may be present at a concentration of 0% (w/w) to about 5% (w/w) of the composition. Examples of antimicrobial agents include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Useful antibacterial zeolites and their preparation are disclosed in U.S. Pat. Nos. 4,911,899 and 4,775,585, each of which is expressly incorporated by reference herein in its entirety.

Any combination of components (E1), (E2), (E3) and (E4) can be incorporated into the inventive composition.

In addition to the previously described components, other components may also be included in various embodiments of the inventive composition. As one example, a component that absorbs ultraviolet light (UV absorber) may be added to improve the color stability of the composition upon exposure to UV light. An example of a UV absorber is 2-hydroxy-4-methoxybenzophenone ("UV-9"). As another example, a flavoring agent or fragrance may be added to impart a pleasant taste and/or smell.

Components (B) and (C) form a redox initiator system that initiates polymerization and hardening of the composition when components (B) and (C) are homogeneously mixed together. The composition can be conveniently packaged into two parts with one part containing component (B) and the other part containing component (C). Components (A), (D), and (E) can be incorporated into either or both parts. The two parts are homogeneously mixed just prior to application of the composition to the tooth. The composition can be a two-part self-cure composition (i.e. curing without the activation of light), or a two-part dual-cure composition (both self-cure and photo-cure) when a photoinitiator is also included. When the two parts are mixed and self-cured (without photo-curing), the mixed composition sets (or hardens) within about 20 minutes. In embodiments, the mixed composition sets within 15 minutes, or within 10 minutes, from the start of mixing. Each part of the two-part composition is independently selected from a liquid, a paste, or a powder. In one embodiment, both parts are in paste forms. In another embodiment, one part is in a liquid form, and the other part is in a powder form. In one embodiment, one part is in a paste form and the other part is in a powder form. In one embodiment, one part is in a paste form and the other part is in a liquid form. One embodiment is a two-part paste/paste composition with the first paste containing components (A) (which may be designated A1), (B), (D) (which may be designated D1), and optionally one or more E1-E4 components; and the second paste containing components (A) (which may be designated A2), (C), (D) (which may be designated D2), and optionally one or more E1-E4 components. Each of the two parts contains 10% (w/w) to 80% (w/w) of at least one polymerizable monomer having at least one vinyl, acrylate, or methacrylate as an ethylenically unsaturated group, and each part contains 15% (w/w) to 90% (w/w) of a finely divided filler. One embodiment is a two-part powder/liquid composition with the liquid part comprising (A) 20% (w/w) to 99.5% (w/w) of at least one polymerizable monomer having at least one ethylenically unsaturated vinyl, acrylate, or methacrylate group; and (C) 0.01% (w/w) to 10% (w/w) of at least one hydroperoxide compound with at least one hydroperoxide group attached to a tertiary carbon; and the powder part comprising (B) 0.01% (w/w) to 10% (w/w) of at least one compound of structure

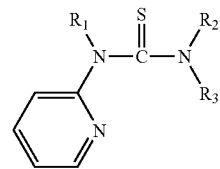

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N; and (D) 50% (w/w) to 99.5% (w/w) of at least one finely divided filler; the composition optionally further comprising 0% (w/w) to 25% (w/w) of a component selected from the group consisting of a photoinitiator, a stabilizer, a solvent, and/or an antimicrobial agent.

The inventive composition can be used as a permanent dental cement, a provisional dental cement, a core buildup material, a dental filling material, a provisional crown and/or bridge material, or an endodontic sealing and/or filling material. The inventive composition improves compatibility with an acidic primer/adhesive.

The invention also includes a dental cementation or core buildup kit comprising the dental cement or core buildup composition comprising components (A), (B), (C), (D), and (E), and an acidic primer/adhesive composition having a pH less than 4.5. The kit may include directions for use. The dental cement or core buildup composition has enhanced compatibility with the acidic primer/adhesive composition so that an improvement in adhesion to a tooth can be realized.

The dental cement or core-buildup composition in the above-described kit has two parts. The two-part composition can be a paste/paste two-part composition, a powder/liquid two-part composition, a liquid/paste two-part composition, or a powder/paste two-part composition. The two-part composition can be provided in prepackaged container(s) such as a syringe, bottle, capsule, ampule, or jar. In one embodiment, the prepackaged container is a dual-syringe assembly. For the dual-syringe assembly, each syringe has an opening and a static mixer is attached to the openings to provide a homogeneous mixture upon dispensing the mixed composition from an exit of the mixer. In another embodiment, the prepackaged container is a single-dose assembly. The above described dual-syringe assembly may be a single-dose assembly. The single-dose assembly may be a capsule that houses a two-part powder/liquid composition, and the content of the capsule can be conveniently mixed by a mechanical mixing device. An example of mechanical mixing device is an amalgamator. The single-dose package may be a blister package that houses a two-part paste/paste composition.

In the above-described kit, the primer/adhesive composition has a pH less than 4.5. In embodiments, the pH is less than 4.0, or less than 3.5, or less than 3.0. The pH value is measured with pH paper. The primer/adhesive composition comprises a minimum of (a) an acidic compound, (b) a polymerizable monomer having at least one ethylenically unsaturated acrylate, methacrylate, or vinyl group, and (c) a solvent of one or more of acetone, ethanol, methanol, water, and/or methyl ethyl ketone. The acidic compound (a) has one or more acidic moieties selected from nitric acid, carboxylic acid, carboxylic acid anhydride, phosphonic acid or its derivative(s), phosphoric acid or its derivative(s), sulfonic acid, and sulfinic acid. In one embodiment, the acidic compound (a) is a polymerizable monomer having at least one acidic moiety and at least one ethylenically unsaturated acrylate, methacrylate, or vinyl group. In one embodiment, the polymerizable monomer (b) is a hydroxyl-containing polymerizable monomer, examples of which include, but are not limited to, hydroxyethyl (meth)acrylate, hydroxypropyl (meth)acrylate, hydroxybutyl (meth)acrylate, glycerol di(meth)acrylate, glycerol mono(meth)acrylate, and/or 2,2-bis[4-(2-hydroxy-3-methacryloylpropoxy)-phenyl]-propane (Bis-GMA). The primer/adhesive composition also contains one or more components selected from a polymerization initiator system, a stabilizer, a finely divided filler, or an antimicrobial agent. The polymerization initiator may be a redox initiator system, a photoinitiator system, or a combination of a redox initiator system and a photoinitiator system.

The primer/adhesive composition may be a single-part system where all components are combined. The primer/adhesive composition may be divided into two or more parts. The primer/adhesive composition may be packaged in a plastic bottle(s) or in a single-dose container(s). In a multi-part configuration, the different parts may be applied sequentially to a prepared tooth surface. Alternatively, all parts may be combined and homogeneously mixed before being applied to a prepared tooth surface.

In another embodiment, the dental cementation or core buildup kit optionally further comprises an acidic etchant, a silane primer, and/or a metal primer. An acidic etchant may be a phosphoric acid, maleic acid, or citric acid etchant used to etch the tooth structure (dentin or enamel). An acidic etchant may also be a hydrofluoric acid etchant used to etch the ceramic substrate of a prosthetic device. A silane primer may be used to prime the ceramic substrate of a prosthetic device to enhance adhesion. A metal primer may be used to prime the metal alloy substrate of a prosthetic device to enhance adhesion.

The invention also discloses a method of adhering a prosthetic device to a tooth to restore the function and/or appearance of a diseased tooth. The prosthetic device includes a dental crown, bridge, inlay, onlay, veneer, or post. A diseased tooth may be prepared (e.g., cleaned, trimmed, cut, etc.) to receive the prosthetic device. Optionally, an acidic etchant may be applied to a tooth and then removed (e.g., by rinsing the etchant off). A primer/adhesive with a pH less than 4.5 is applied to the tooth surface receiving the prosthetic device, and the prosthetic device is adhered to the primer/adhesive coated tooth surface using the inventive dental cement composition. The cement composition is then hardened. In one embodiment, the primer/adhesive has a pH less than 4.0. In one embodiment, the primer/adhesive has a pH less than 3.5. In one embodiment, the primer/adhesive has a pH less than 3.0. The method results in enhanced adhesion of the prosthetic device due to the acid tolerant nature of the dental cement composition, resulting in enhanced compatibility with the acidic primer/adhesive.

The two-part paste/paste, powder/liquid, or paste/liquid composition may be used as a provisional or temporary dental material. The duration of a provisional or temporary material is typically less than three months before a permanent dental restorative material is placed. The temporary dental material may be a temporary cement, a temporary crown and/or bridge, a temporary inlay, or a temporary onlay. The composition may also be used as an endodontic sealer and/or endodontic filling material. In a method using the two-part composition as a provisional dental material or as an endodontic material, the two-part composition (components (A), (B), (C), (D) and (E)) is prepared. The tooth is prepared. The two parts of the two-part composition are mixed just prior to application, then the mixed composition is applied to the tooth and the composition is hardened. In this embodiment for provisional or endodontic application, one type of polymerizable monomer is an elastomeric (meth)acrylate oligomer. The elastomeric (meth)acrylate oligomer may be an elastomeric urethane (meth)acrylate oligomer and/or an elastomeric polyalkyleneglycol (meth)acrylate oligomer. Those elastomeric oligomers are disclosed in U.S. Pat. No. 6,353,041 which is expressly incorporated by reference herein in its entirety.

The invention also discloses a method of using a core buildup material to build up a tooth structure, or replace missing dentition, to receive a crown. The method involves the steps of (1) preparing the tooth to receive the core buildup material (e.g., cutting and cleaning); (2) optionally, etching the prepared tooth with an acid etchant and rinsing to remove the etchant; (3) applying a acidic primer/adhesive to coat the tooth surface to receive the core buildup material; (4) placing the core buildup material onto the primer/adhesive coated tooth surface; and (5) hardening the core-buildup material.

The following examples illustrate how current invention is applied and should not limit the scope of the invention.

Flexural Strength (FS)

FS was measured from the same flexural test according to an ISO 4049 standard. The specimens were prepared by condensing the mixed paste into a stainless-steel mold with a dimension of 2 mm×2 mm×25 mm, and then either self-cured or photo-cured from both sides. The cured disk was removed from the mold and conditioned in 37° C. water for 24 hours before subjecting to mechanical testing on an Instron Universal Tester (Model 4202) in 3-point bending mode with a crosshead speed of 0.5 mm/minute. The peak load at which the specimen breaks is used to calculate the FS, expressed in MPa unit. Six specimens were tested for each formula.

EXAMPLES

The following abbreviations for materials are used in all examples.

Barium Glass: bariumaluminoborosilicate filler that has a mean particle size of one micron and surface treated with MPTMS
BHT: 2,6-di-(tert-butyl)-4-methylphenol
Bis-GMA: 2,2-bis[4-(2-hydroxy-3-methacryloylpropoxy)-phenyl]-propane
CHPO: cumene hydroperoxide
CQ: camphoroquinone
EDMAB: ethyl 4-(N,N-dimethylamino) benzoate
ETMPTA: ethoxylated trimethylolpropane triacrylate with 3 moles of ethylene oxide
GDM: glyceryldimethacrylate
GDM-P: glyceryldimethacrylate phosphate
HEMA: hydroxyethyl methacrylate
MEHQ: 4-methoxyphenol
MPTMS: γ-methacryloyloxypropyltrimethoxysilane
ODMAB: 2-(ethylhexyl)-4-(N,N-dimethylamino) benzoate
PTU: 1-(2-pyridyl)-2-thiourea
Sr/Zn FAS Glass: strontiumzincfluoroaluminosilicate glass that has a mean particle size of four microns and surface treated with MPTMS
ST-OX-50: fumed silica OX-50 surface treated with MPTMS
TMBHPO: 1,1,3,3-tetramethylbutyl hydroperoxide
TS-530: surface treated fumed silica or colloidal silica sold by Cabot Corp.
UDMA: reaction product of 2-hydroxyethyl methacrylate with 2,4,4-trimethylhexane diisocyanate

Example 1

In making the pastes in this and the following examples, all the monomers and any ingredients soluble in the resin mixture were first mixed together to make a homogeneous liquid mixture, and then the fillers (TS-530, ST-OX-50, Sr/Zn FAS glass, or barium glass) were blended into the liquid mixture to make the paste.

An acid tolerant cement was made using the following composition.

| Base | |
|---|---|
| BisGMA | 17.10 |
| GDM | 8.55 |
| HEMA | 5.13 |
| ETMPTA | 3.41 |
| CQ | 0.21 |
| MEHQ | 0.007 |
| ODMAB | 0.41 |
| PTU | 0.68 |
| TS-530 | 3.00 |
| ST-OX-50 | 3.34 |
| Barium Glass | 58.16 |
| Catalyst | |
| BisGMA | 9.70 |
| GDM | 9.70 |
| HEMA | 4.84 |
| GDM-P | 4.84 |
| ETMPTA | 3.24 |
| BHT | 0.05 |
| TMBHPO | 0.29 |
| CHPO | 0.58 |
| Water | 2.26 |
| TS-530 | 3.00 |
| ST-OX-50 | 3.34 |
| Barium Glass | 58.16 |

When the base paste and catalyst paste were mixed at 1:4 ratio, the mixed material hardened (or set) after 4 minutes and 20 seconds. The self-cured (dark-cured) material had a flexural strength of 80.7 MPa, and a radiopacitiy that was 170% of aluminum.

Example 2

An adhesion test to a dentin substrate was conducted on a commercial Panavia® F2.0 cementation system (Kuraray America, Inc., New York N.Y.). The Panavia® F2.0 cementation kit comprised two self-etching Primers (Primer A and Primer B) and a resin cement. Primer A and Primer B were packaged in two separate plastic bottles. The cement consisted of two pastes (base and catalyst pastes) packaged in two separate individual syringes.

The bonding strength was conducted as follows: The dentin surface was polished with wet 600 grit SiC paper. The primers were mixed at 1:1 ratio and the mixed primer was applied to dentin using a brush (separate acid etching was not necessary because the primers were self-etching). The pH of the mixed primers was 2.7 measured using pH paper. The primer was left on the dentin for 30 seconds and then the solvent was evaporated using compressed air for 2-3 seconds. A plastic mold with an inner diameter of 2.38 mm was securely placed over the primed tooth surface. The cement was dispensed from the syringes and homogeneously mixed. The mixed cement was condensed inside the mold and intimately bonded to the primer. The cement was self-cured (or dark-cured) for 24 hours. The bond strength was tested on an Instron mechanical tester using shear force. A bond strength of 11.7 MPa was obtained.

The above bond strength test was repeated using the self-etching primers of Panavia® F2.0 and acid tolerant cement of Example 1 replacing the cement of Panavia® F2.0. The base paste and catalyst pastes of Example 1 were mixed in 1:4 (base paste:catalyst paste) ratio. A bond strength of 23.3 MPa was obtained. The enhanced bond strength over that obtained with Panavia® F2.0 primers and cement demonstrated the acid tolerant nature of the cement of Example 1 and enhanced compatibility between the acidic primers of Panavia® F2.0 and the cement of Example 1.

Example 3

An adhesion test to a dentin substrate was conducted on another commercial cementation system, Multilink® (Ivoclar Vivadent Inc., Amherst, N.Y.). The Multilink® cementation kit comprised two self-etching Primers (Primer A and Primer B) and a resin cement. Primer A and Primer B were packaged in two separate plastic bottles. The cement consisted of two pastes (base and catalyst pastes) packaged in separate barrels of a dual-barrel assembly. The bonding strength was conducted in the same manner as described in Example 2. The primers were mixed at 1:1 ratio and the mixed primer was applied to dentin using a brush (the pH of the mixed primers was 2.5 measured using pH paper). The primer was left on dentin for 15 seconds and then the solvent was evaporated using compressed air for 2-3 seconds. A plastic mold with an inner diameter of 2.38 mm was securely placed over the primed tooth surface. The cement was dispensed from the dual-barrel assembly and homogeneously mixed. The mixed cement was condensed inside the mold and intimately bonded to the primer. The cement was self-cured (or dark-cured) for 24 hours. The bond strength was tested on an Instron mechanical tester using shear force. A bond strength of 17.8 MPa was obtained.

The above described bond strength test was repeated using the self-etching primers of Multilink® and the acid tolerant cement of Example 1 replacing the cement of Multilink®. The base paste and catalyst pastes of Example 1 were mixed in 1:4 (base paste:catalyst paste) ratio. A bond strength of 23.4 MPa was obtained. The enhanced bond strength over that obtained with Multilink® primers and cement demonstrated the acid tolerant nature of the cement of Example 1 and enhanced compatibility between the acidic primers of Multilink® and the cement of Example 1.

Example 4

An acid tolerant cement was made using the following composition:

| Base | |
|---|---|
| UDMA | 21.35 |
| GDM | 4.27 |
| HEMA | 2.85 |
| CQ | 0.142 |
| MEHQ | 0.014 |
| EDMAB | 0.285 |
| PTU | 0.59 |
| TS-530 | 3.00 |
| ST-OX-50 | 4.72 |
| Sr/Zn FAS Glass | 62.78 |
| Catalyst | |
| BisGMA | 5.56 |
| GDM | 7.29 |
| HEMA | 2.78 |
| ETMPTA | 3.47 |
| GDM-P | 12.16 |
| BHT | 0.05 |
| TMBHPO | 0.63 |
| CHPO | 0.63 |
| Water | 2.43 |
| TS-530 | 3.00 |
| ST-OX-50 | 1.60 |
| Barium Glass | 60.40 |

When the base paste and catalyst paste were mixed at 1:4 ratio, the mixed material hardened (or set) after 4 minutes and 30 seconds. The self-cured (dark-cured) material had a flexural strength of 83.0 MPa, and a radiopacitiy that was 200% of aluminum.

Example 5

A commercial dental primer, OptiBond® Primer (Kerr Corporation, Orange, Calif.), was used for an adhesion test in combination with a commercial resin cement Nexus 2™ Dual-Syringe (Kerr Corporation, Orange, Calif.) or the acid tolerant resin cement composition of Example 4. OptiBond® Primer was a single primer (one-bottle) system and had a pH of 1.9. Resin cement Nexus 2™ Dual-Syringe utilized benzoyl peroxide/tertiary amine as its redox initiator system. The base and catalyst pastes of Nexus 2™ Dual-Syringe were packaged in the separate barrels of a dual-barrel assembly (1:1 ratio). The bonding strength was conducted as follows: the dentin surface was polished with wet 600 grit SiC paper, etched with a 37% Phosphoric Acid Gel Etchant (Kerr Corporation, Orange, Calif.) for 15 seconds. The surface was then rinsed with water and briefly dried with compressed air. OptiBond® Primer was applied to the etched tooth surface with agitation using a brush for 30 seconds and then the solvent was evaporated using compressed air for 3-5 seconds. A plastic mold with an inner diameter of 2.38 mm was securely placed over the primed tooth surface. The Nexus 2™ Dual-Syringe resin cement was dispensed from the dual-barrel assembly fitted with a static mixer. The mixed cement was condensed inside the mold and intimately bonded to the primer. The cement was self-cured (or dark-cured) for 24 hours. The bond strength was tested on an Instron mechanical tester using shear force. A bond strength of 10.4 MPa was obtained.

The above bond strength test was repeated using the OptiBond® Primer and acid tolerant cement of Example 4 replacing the resin cement Nexus 2™ Dual-Syringe. The base paste and catalyst pastes of Example 4 were mixed in 1:4 (base paste:catalyst paste) ratio. A bond strength of 26.0 MPa was obtained. The enhanced bond strength over that obtained with OptiBond® Primer+Nexus 2™ Dual-Syringe resin cement demonstrated the acid tolerant nature of the cement composition of Example 4 and enhanced compatibility between the acidic OptiBond® Primer and the cement composition of Example 4. An example of a dental cementation kit would include Phosphoric Acid Gel Etchant in this example, OptiBond® Primer in this example, and the acid-tolerant cement composition of Example 4.

The above examples demonstrate the usefulness of the acid-tolerant resin cement of the invention in enhancing adhesion of acidic primer/adhesives to a tooth substrate due to improved compatibility between the resin cement of the invention and an acidic primer/adhesive.

The above examples are for illustration only, and should not be construed to limit the scope of this invention. Other variations or embodiments of the invention will also be apparent to one of ordinary skill in the art from the above description and examples. Thus, the forgoing embodiments are not to be construed as limiting the scope of the claimed invention.

What is claimed is:

1. A method for adhering a prosthetic device to a tooth comprising
    (1) applying a primer/adhesive with a pH less than 4.5 to a surface of a tooth prepared to receive a prosthetic device, wherein the primer/adhesive comprises (a) an acidic compound, (b) a polymerizable monomer having at least one ethylenically unsaturated group selected from the group consisting of vinyl, acrylate, and methacrylate, and (c) at least one solvent selected from the group consisting of acetone, ethanol, methanol, water, and methyl ethyl ketone,
    (2) adhering the prosthetic device to the primer/adhesive coated tooth surface using a dental cement composition, and
    (3) hardening the dental cement composition,
    wherein the dental cement composition is a two-part composition which comprises
    (A) 5% (w/w) to 90% (w/w) of at least one polymerizable monomer having at least one ethylenically unsaturated group selected from the group consisting of vinyl, acrylate, and methacrylate;
    (B) 0.01% (w/w) to 10% (w/w) of at least one compound of structure

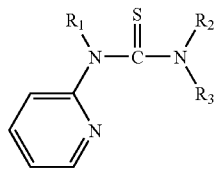

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N;
    (C) 0.01% (w/w) to 10% (w/w) of at least one hydroperoxide compound with at least one hydroperoxide group attached to a tertiary carbon;
    (D) 5% (w/w) to 95% (w/w) of at least one finely divided filler having a mean particle size less than 50 microns; and
    (E) 0% (w/w) to 25% (w/w) of at least one component selected from the group consisting of a solvent, a photoinitiator, a stabilizer, an antimicrobial agent, and combinations thereof,
    wherein component (B) is in a first part of the two-part composition, component (C) is in a second part of the two-part composition, and components (A), (D), and (E) are independently in either the first part and/or the second part
        wherein the at least one compound of component (B) does not include 1-(2-pyridyl)-2-thiourea.

2. The method of claim 1 wherein each of R1, R2, and R3 is independently selected from the group consisting of H, alkyl, alkoxyl, phenyl, 2-pyridyl, 2-tetrahydrofurfuryl, acetyl, and benzoyl.

3. The method of claim 1 wherein the hydroperoxide compound is selected from the group consisting of t-butyl hydroperoxide, t-amyl hydroperoxide, p-diisopropylbenzene hydroperoxide, cumene hydroperoxide, pinane hydroperoxide, p-menthane hydroperoxide, 1,1,3,3-tetramethylbutyl hydroperoxide, and combinations thereof.

4. The method of claim 1 wherein at least one of the polymerizable monomers of component (A) contains a functional group selected from the group consisting of a hydroxyl group, an acid group, and combinations thereof.

5. The method of claim 4 wherein the hydroxyl-containing polymerizable monomer is selected from the group consisting of hydroxyethyl (meth)acrylate, hydroxypropyl (meth)acrylate, glycerol di(meth)acrylate, glycerol mono(meth)acrylate, 2,2-bis[4-(2-hydroxy-3-methacryloylpropoxy)-phenyl]-propane (Bis-GMA), and combinations thereof.

6. The method of claim 4 wherein the acid group is selected from the group consisting of carboxylic acid, carboxylic acid anhydride, sulfonic acid, sulfinic acid, phosphoric acid, phosphoric acid derivative, phosphonic acid, and phosphonic acid derivative.

7. The method of claim 1 wherein the filler is selected from the group consisting of inorganic metal, salt, oxide, nitride, silicate glass, bariumaluminosilicate glass, bariumaluminoborosilicate glass, strontiumaluminosilicate glass, bariumfluoroaluminosilicate glass, strontiumfluoroaluminosilicate glass, strontiumzincfluoroaluminosilicate glass, zincaluminosilicate glass, quartz, colloidal silica, precipitated silica, zirconia-silica, polymeric filter, polymerized composite filler with inorganic particles, and combinations thereof.

8. The method of claim 1 wherein the solvent is selected from the group consisting of water, acetone, methanol, ethanol, isopropanol, methyl ethyl ketone, ethylene glycol, glycerin, and combinations thereof.

9. The method of claim 1 wherein the antimicrobial agent is selected from the group consisting of benzalkonium chloride, triclosan, alkyl 4-hydroxybenzoate, zinc oxide, silicate glass powder containing silver and/or zinc, zeolite containing silver and/or zinc ion(s), and combinations thereof.

10. The method of claim 1 wherein the pH of the primer/adhesive is less than 3.0.

11. The method of claim 1 further comprising applying an acidic etchant to the tooth surface and thereafter rinsing the surface to remove the etchant prior to step (1).

12. A method for providing a tooth with a dental composition, the method comprising
    (1) providing to a tooth a dental composition which is a two-part composition comprising
    (A) 5% (w/w) to 90% (w/w) of at least one polymerizable monomer having at least one ethylenically unsaturated group selected from the group consisting of vinyl, acrylate, and methacrylate;
    (B)) 0.01% (w/w) to 10% (w/w) of at least one compound of structure

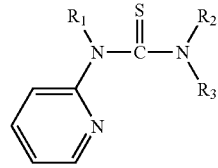

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N;
    (C) 0.01% (w/w) to 10% (w/w) of at least one hydroperoxide compound with at least one hydroperoxide group attached to a tertiary carbon;

(D) 5% (w/w) to 95% (w/w) of at least one finely divided filler having a mean particle size less than 50 microns; and (E) 0% (w/w) to 25% (w/w) of at least one component selected from the group consisting of a solvent, a photoinitiator, a stabilizer, an antimicrobial agent, and combinations thereof;

wherein (i) component (B) is in a first part of the two-part composition, (ii) component (C) is in a second part of the two-part composition, (iii) components (A), (D), and (E) are independently in either the first part and/or the second part, and (iv) the parts are mixed before application to the tooth, and (2) thereafter hardening the dental composition;
wherein the at least one compound of component (B) does not include 1-(2-pyridyl)-2-thiourea.

13. The method of claim 12 wherein the dental composition provided to the tooth is at least one of a permanent cement, a core build-up material, a filling material, an endodontic sealer, an endodontic filling material, a temporary cement, a temporary crown and/or bridge, a temporary inlay, or a temporary onlay.

14. The method of claim 12 wherein each of R1, R2, and R3 may be the same or different and is independently selected from the group consisting of H, alkyl, alkoxyl, phenyl, 2-pyridyl, 2-tetrahydrofurfuryl, acetyl, and benzoyl.

15. The method of claim 12 wherein the hydroperoxide compound is selected from the group consisting of t-butyl hydroperoxide, t-amyl hydroperoxide, p-diisopropylbenzene hydroperoxide, cumene hydroperoxide, pinane hydroperoxide, p-menthane hydroperoxide, 1,1,3,3-tetramethylbutyl hydroperoxide, and combinations thereof.

16. The method of claim 12 wherein the filler is selected from the group consisting of inorganic metal, salt, oxide, nitride, silicate glass, bariumaluminosilicate glass, bariumaluminoborosilicate glass, strontiumaluminosilicate glass, bariumfluoroaluminosilicate glass, strontiumfluoroaluminosilicate glass, strontiumzincfluoroaluminosilicate glass, zincaluminosilicate glass, quartz, colloidal silica, precipitated silica, zirconia-silica, polymeric filler, polymerized composite filler with inorganic particles, and combinations thereof.

17. The method of claim 12 wherein the solvent is selected from the group consisting of water, acetone, methanol, ethanol, isopropanol, methyl ethyl ketone, ethylene glycol, glycerin, and combinations thereof.

18. The method of claim 12 wherein the antimicrobial agent is selected from the group consisting of benzalkonium chloride, triclosan, alkyl 4-hydroxybenzoate, zinc oxide, silicate glass powder containing silver and/or zinc, zeolite containing sliver and/or zinc ion(s), and combinations thereof.

19. The method of claim 12 wherein at least one polymerizable monomer is an elastomeric (meth)acrylate oligomer selected from the group consisting of elastomeric urethane (meth)acrylate oligomer and elastomeric polyalkyleneglycol (meth)acrylate oligomer.

20. A method for providing a tooth with a dental composition, the method comprising (1) applying an acidic primer/adhesive with a pH less than 4.5 to a tooth surface, wherein the primer/adhesive comprises (a) an acidic compound, (b) a polymerizable monomer having at least one ethylenically unsaturated group selected from the group consisting of vinyl, acrylate, and methacrylate, and (c) at least one solvent selected from the group consisting of acetone, ethanol, methanol, water, and methyl ethyl ketone, (2) placing the dental composition on the primer/adhesive coated tooth surface, and (3) hardening the dental composition, wherein the dental composition is a two-part composition which comprises (A) 5% (w/w) to 90% (w/w) of at least one polymerizable monomer having at least one ethylenically unsaturated group selected from the group consisting of vinyl, acrylate, and methacrylate;

(B) 0.01% (w/w) to 10% (w/w) of at least one compound of structure

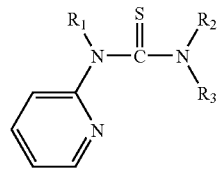

where each of R1, R2, and R3 may be the same or different and is independently selected from the group consisting of H, alkyl, alkoxyl, aryl, acyl, allyl, pyridyl, —OH, alkenyl, aralkyl, cycloalkyl, and heterocyclic structure containing O, S, or N;

(C) 0.01% (w/w) to 10% (w/w) of at least one hydroperoxide compound with at least one hydroperoxide group attached to a tertiary carbon;

(D) 5% (w/w) to 95% (w/w) of at least one finely divided filler having a mean particle size less than 50 microns; and (E) 0% (w/w) to 25% (w/w) of at least one component selected from the group consisting of a solvent, a photoinitiator, a stabilizer, an antimicrobial agent, and combinations thereof;

wherein component (B) is in a first part of the two-part composition, component (C) is in a second part of the two-part composition, and components (A), (D), and (E) are independently in either the first part and/or the second part wherein the at least one compound of component (B) does not include 1-(2-pyridyl)-2-thiourea.

21. The method of claim 20 wherein each of R1, R2, and R3 is independently selected from the group consisting of H, alkyl, alkoxyl, phenyl, 2-pyridyl, 2-tetrahydrofurfuryl, acetyl, and benzoyl.

22. The method of claim 20 wherein the hydroperoxide compound is selected from the group consisting of t-butyl hydroperoxide, t-amyl hydroperoxide, p-diisopropylbenzene hydroperoxide, cumene hydroperoxide, pinane hydroperoxide, p-menthane hydroperoxide, 1,1,3,3,-tetramethylbutyl hydroperoxide, and combinations thereof.

23. The method of claim 20 wherein at least one of the polymerizable monomers of components (A) contains a functional group selected from the group consisting of a hydroxyl group, an acid group, and combinations thereof.

24. The method of claim 23 wherein the hydroxyl-containing polymerizable monomer is selected from the group consisting of hydroxyethyl (meth)acrylate, hydroxypropyl (meth)acrylate, glycerol di(meth)acrylate, glycerol mono (meth)acrylate, 2,2-bis[4-(2-hydroxy-3-methacryloylpropoxy)-phenyl]-propane (Bis-GMA), and combinations thereof.

25. The method of claim 23 wherein the acid group is selected from the group consisting of carboxylic acid, carboxylic acid anhydride, sulfonic acid, sulfonic acid, phosphoric acid, phosphoric acid derivative, phosphonic acid, phosphonic acid derivative, and combinations thereof.

26. The method of claim 20 wherein the filler is selected from the group consisting of inorganic metal, salt, oxide, nitride, silicate glass, bariumaluminosilicate glass, bariumaluminoborosilicate glass, strontiumaluminosilicate glass, bariumfluoroaluminosilicate glass, strontiumfluoroaluminosilicate glass, strontiumzincfluoroaluminosilicate glass, zincaluminosilicate glass, quartz, colloidal silica, precipitated silica, zirconia-silica, polymeric filer, polymerized composite filler with inorganic particles, and combinations thereof.

27. The method of clam 20 wherein the solvent is selected from the group consisting of water, acetone, methanol, ethanol, isopropanol, methyl ethyl ketone, ethylene glycol, glycerin, and combinations thereof.

28. The method of claim 20 wherein the antimicrobial agent is selected from the group consisting of benzalkonium chloride, triclosan, alkyl 4-hydroxybenzoate, zinc oxide, silicate glass powder containing silver and/or zinc, zeolite containing silver and/or zinc ion(s), and combinations thereof.

29. The method of claim 20 wherein the pH of the primer/adhesive is less than 3.0.

30. The method of claim 20 further comprising applying an acidic etchant to the tooth surface and thereafter rinsing the surface to remove the etchant prior to step (1).

31. The method of claim 20 wherein the dental composition is selected from the group consisting of a core buildup material, a filling material, an endodontic sealer, an endodontic filling material, and combinations thereof.

32. The method of claim 1 wherein the antimicrobial agent is triclosan which is present in an amount up to 5% (w/w).

33. The method of claim 1 wherein the antimicrobial agent is zeolite containing silver and/or zinc which is present in an amount up to 5% (w/w).

34. The method of claim 1 wherein the antimicrobial agent is zeolite containing silver and/or zinc which is present in an amount of 0.5% (w/w).

35. The method of claim 1 wherein the at least one compound is present in an amount ranging from 0.5% (w/w) to 2% (w/w).

36. The method of claim 1 wherein the at least one compound is present in an amount ranging from 0.1% (w/w) to 1% (w/w).

37. The method of claim 1 wherein the acidic compound is a polymerizable monomer having at least one acidic moiety and at least one ethylenically unsaturated acrylate, methacrylate, or vinyl group.

38. The method of claim 12 wherein the antimicrobial agent is triclosan which is present in an amount up to 5% (w/w).

39. The method of claim 12 wherein the antimicrobial agent is zeolite containing silver and/or zinc which is present in an amount up to 5% (w/w).

40. The method of claim 12 wherein the antimicrobial agent is zeolite containing silver and/or zinc which is present in an amount of 0.5% (w/w).

41. The method of claim 12 wherein the at least one compound is present in an amount ranging from 0.5% (w/w) to 2% (w/w).

42. The method of claim 12 wherein the at least one compound is present in an amount ranging from 0.1% (w/w) to 1% (w/w).

43. The method of claim 20 wherein the antimicrobial agent is triclosan which is present in an amount up to 5% (w/w).

44. The method of claim 20 wherein the antimicrobial agent is zeolite containing silver and/or zinc which is present in an amount up to 5% (w/w).

45. The method of claim 20 wherein the antimicrobial agent is zeolite containing silver and/or zinc which is present in an amount of 0.5% (w/w).

46. The method of claim 20 wherein the at least one compound is present in an amount ranging from 0.05% (w/w) to 2% (w/w).

47. The method of claim 20 wherein the at least one compound is present in an amount ranging from 0.1% (w/w) to 1% (w/w).

48. The method of claim 20 wherein the acidic compound is a polymerizable monomer having at least one acidic moiety and at least one ethylenically unsaturated acrylate, methacrylate, or vinyl group.

49. The method of claim 1, wherein the prosthetic device is metal-based or opaque.

50. The method of claim 1, wherein the hardening the dental composition comprises self-curing and photo-curing.

51. The method of claim 12, wherein the hardening the dental composition comprises self-curing and photo-curing.

52. The method of claim 20, wherein the hardening the dental composition comprises self-curing and photo-curing.

* * * * *

UNITED STATES PATENT AND TRADEMARK OFFICE
CERTIFICATE OF CORRECTION

| | | |
|---|---|---|
| PATENT NO. | : 7,498,367 B2 | Page 1 of 1 |
| APPLICATION NO. | : 10/906447 | |
| DATED | : March 3, 2009 | |
| INVENTOR(S) | : Qian | |

It is certified that error appears in the above-identified patent and that said Letters Patent is hereby corrected as shown below:

Title Page, Col. 2, Item (57) ABSTRACT, 6 lines below structure, "least one hydroperoxide groups" should read --least one hydroperoxide group--.

Col. 2, line 41, "2-tetrahydrofufuryl" should read --2-tetrahydrofurfuryl--.

Col. 7, line 57, "1-(2-tetrahydrofufuryl)" should read --1-(2-tetrahydrofurfuryl)--.

Col. 9, line 13, "camphorquinone" should read --camphoroquinone--.

Col. 18, line 23, Claim 17, "polymeric filter" should read --polymeric filler--.

Col. 18, line 47, Claim 12, "(B))" should read --(B)--.

Col. 19, line 50, Claim 18, "sliver" should read --silver--.

Col. 20, line 65, Claim 25, "sulfonic acid, sulfonic acid" should read --sulfonic acid, sulfinic acid--.

Col. 21, line 8, Claim 26, "polymeric filer" should read --polymeric filler--.

Signed and Sealed this

Nineteenth Day of January, 2010

David J. Kappos
*Director of the United States Patent and Trademark Office*